United States Patent [19]

Takada et al.

[11] Patent Number: 4,717,506
[45] Date of Patent: Jan. 5, 1988

[54] PYRAN DERIVATIVES AND PERFUME COMPOSITION CONTAINING THE SAME

[75] Inventors: Hiroshi Takada; Shin'ichi Masuda, both of Wakayama; Motoki Nakajima, Saitam, all of Japan

[73] Assignee: Kao Corporation, Tokyo, Japan

[21] Appl. No.: 821,456

[22] Filed: Jan. 22, 1986

[30] Foreign Application Priority Data

Jan. 23, 1985 [JP] Japan .................. 60-10516

[51] Int. Cl.$^4$ .................. A61K 7/46; C07D 309/18
[52] U.S. Cl. .................. 512/11; 549/356
[58] Field of Search .................. 549/356; 252/522 R

[56] References Cited

U.S. PATENT DOCUMENTS

| | | | |
|---|---|---|---|
| 2,422,648 | 6/1947 | Williams et al. | 549/356 |
| 4,221,679 | 9/1980 | Willis et al. | 549/356 |
| 4,560,776 | 12/1985 | Boden | 549/356 |

*Primary Examiner*—Nicky Chan
*Attorney, Agent, or Firm*—Birch, Stewart, Kolasch & Birch

[57] ABSTRACT

The present invention relates to a novel pyran derivative mixture represented by the following general formula (I):

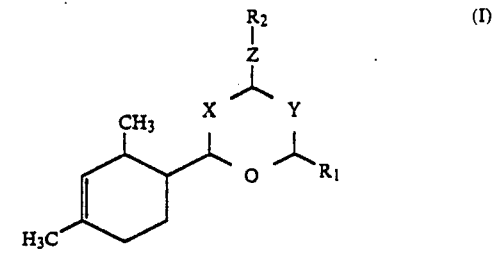

wherein $R_1$ is H or $CH_3$, $R_2$ is $CH_2$ or $CH_3$, one of the bonds X, Y, or Z is a double bond and the remaining two bonds are single bonds. The present invention relates to a process for the preparation of the above-mentioned pyran derivative mixture. The pyran derivative compound (I) of the present invention is produced by reacting a compound represented by the following formula (II):

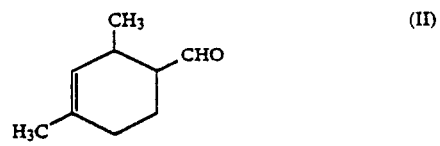

with a compound represented by the general formula (III):

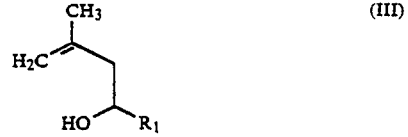

in the presence of an acid catalyst wherein $R_1$ is as defined above. In addition, the present invention relates to a perfume composition containing an effective aromal amount of the pyran derivative compound represented by the general formula (I) above, in the presence of an acceptable carrier therefore.

4 Claims, 2 Drawing Figures

PYRAN DERIVATIVES AND PERFUME COMPOSITION CONTAINING THE SAME

TECHNICAL FIELD

The present invention relates to perfumes, and particularly to a pyran derivative mixture, a process for making the pyran derivative mixture and a perfume composition containing the noval pyran derivative mixture.

BACKGROUND ART

It is known that 2,4-dimethyl-3-cyclohexene-1-carboxyaldehyde, represented by the following formula (II):

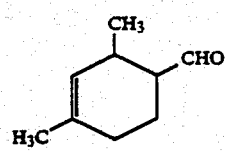

has a strong leaf-like green aroma (see Perfume and Flavor Chemicals I by Steffen Arctander No. 996). However, the compound of the above formula (II) is disadvantageous because it contains a formyl group making it unstable.

SUMMARY OF THE INVENTION

The present invention relates to a novel pyran derivative mixture represented by the following general formula (I):

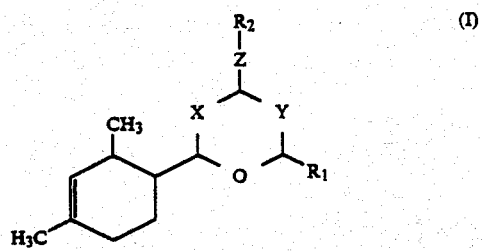

wherein $R_1$ is H or $CH_3$, $R_2$ is $CH_2$ or $CH_3$, one of the bonds X, Y, or Z is a double bond and the remaining two bonds are single bonds.

The present invention also relates to a process for the preparation of the above-mentioned pyran derivative mixture. The pyran derivative compound (I) of the present invention is produced by reacting a compound represented by the following formula (II):

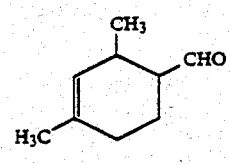

with a compound represented by the general formula (III):

in the presence of an acid catalyst, wherein $R_1$ is as defined above.

In addition, the present invention relates to a perfume composition containing an effective aromal amount of the pyran derivative compound represented by the general formula (I) above, in the presence of an acceptable carrier therefor. Any conventional and suitable carrier may be employed in the perfume composition together with the novel fragrant compounds of the invention.

Accordingly, the present invention provides a novel pyran derivative mixture represented by the general formula (I), a process for the preparation of the pyran derivative mixture, and a perfume composition containing the pyran derivative mixture.

DETAILED DESCRIPTION OF THE INVENTION

Figure 1:
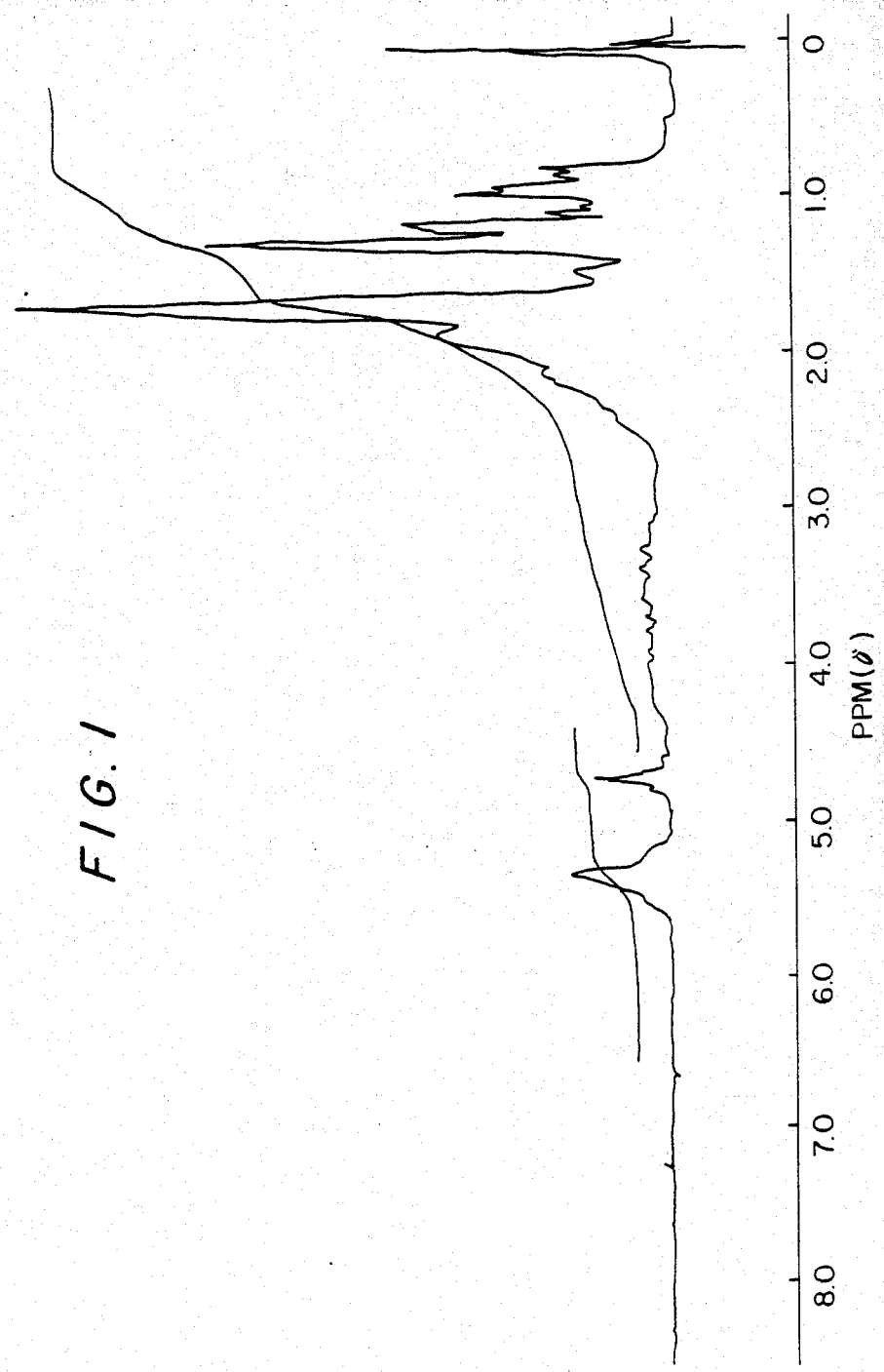
FIG. 1 is a H-NMR spectrum of the product obtained in Example 1.

The inventors have accomplished the present invention as a result of intensive studies to overcome the problem of producing a stable mixture having a leaf green aroma. A pyran derivative mixture represented by the above formula (I) is obtained by reacting compound (II) with a compound represented by the following general formula (III):

wherein $R_1$ is as defined above. The resulting pyran derivative is useful as a raw material for the preparation of perfume compositions because the compound not only has excellent stability, but a persistent and a fresh tomato leaf green aroma.

The pyran derivative (I) of the present invention has the following three isomers, which can be distinguished by the position of the double bond:

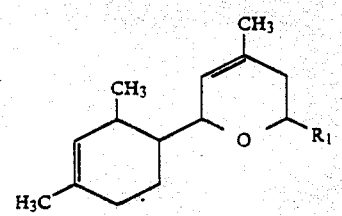

-continued

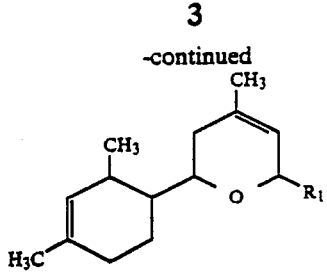
(Ib)

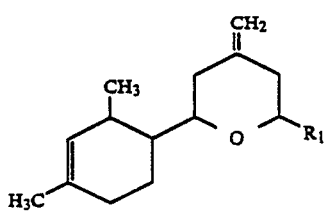
(Ic)

wherein R₁ is as defined above.

The pyran derivative mixture of the present invention can be prepared by reacting, 2,4-dimethyl-3-cyclohexene-1-carboxyaldehyde (II) with compound (III) in the presence of an acid catalyst. For example, the following reaction formula outlines a method for producing a mixture of the three isomers:

(II) + (III) →

(IV) →

(Ia) +

(Ib) +

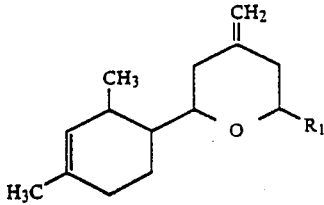
(Ic)

wherein R₁ is as defined above.

In the above process, although the molar ratio of compound (III) to compound (II) is not particularly defined, it is preferred to use 0.5 to 2.0 mol of the compound (III) per mol of the compound (II). A strong acid is preferably used as an acid catalyst. Examples of acids useful as catalysts includes sulfuric, p-toluenesulfonic, hydrochloric, and phosphoric acids. The amount of the catalyst, though it depends on the type of catalyst, is preferably within the range of 0.01 to 10% based on the amount of the starting material.

The reaction is preferably carried out in a solvent which can azeotropically remove water from the reaction system, since the reaction involves dehydration. Hexane, benzene, toluene, xylene, and the like are preferably used as the solvent.

Since an intermediate (IV) is formed in the process of the present reaction, as shown in the above reaction formula, the reaction can be effected either in a one step or in a two step process. The reaction is usually effected at a temperature ranging from 10° to 200° C. If the reaction is effected in one step, the temperature is preferably within the range of 50° to 150° C., more preferably from 60° to 120° C. When the reaction is effected in two steps, it is preferred to conduct the first reaction at 10° to 100° C. and the second reaction at 50° to 150° C. The reaction time which depends on the reaction temperature, usually ranges from about 1 to 200 hours.

The product obtained by this process is in a mixture of (Ia), (Ib), and (Ic). The obtained product is preferably used as a mixture, without separation.

As described heretofore, the compound (I) of the present invention is excellent in stability and has a persistent green perfume aroma like tomato leaf. Accordingly, the present compound can be used for the preparation of various perfume compositions.

The following examples are given merely as illustrative of the present invention and are not to be considered limiting.

EXAMPLE 1

A mixture of 69 g (0.5 mol) of 4-methyl-4-penten-2-ol (72% purity), 69 g (0.5 mol) of 2,4-dimethyl-3-cyclohexene-1-carboaldehyde, and 1 g of p-toluenesulfonic acid was stirred at room temperature for 96 hours. The mixture was then treated with 100 g of an aqueous sodium carbonate solution (5%) and washed with water three times. 100 g of xylene and 0.3 g of concentrated sulfuric acid were added thereto, and the reaction was continued under reflux for 3 hours, the generated water being removed out of the reaction system by azeotropic distillation with xylene. The reaction product was treated with 100 g of an aqueous sodium carbonate solution (5%) and washed with water three times. After the solvent and the low-boiling fractions had been distilled off, the distillation was continued to obtain 79 g of a fraction at 110° to 120° C. at 3.5 mmHg.

The obtained fraction was further subjected to precision distillation, yielding 35 g of a fraction at 106° to 108° at 3.5 mmHg. As the result of the determination of the product by gas chromatography using Carbowax 20M (capillary column 50 m) and gas mass spectroscopy, it was recognized that the product was a mixture of 2,4-dimethyl-6-(2,4-dimethyl-3-cyclohexenyl)-3,6-dihydro-2H-pyran (Ia-CH$_3$), 4,6-dimethyl-2-(2,4-dimethyl-3-cyclohexenyl)-3,6-dihydro-2H-pyran (Ib-CH$_3$), and 2-(2,4-dimethyl-3-cyclohexenyl)-6-methyl-4-methylenetetrahydropyran (Ic-CH$_3$), which are the compounds of the formulae (Ia) to (Ic), wherein R$_1$ is CH$_3$, and the purity of the product was at least 99%. The parent peak was found at m/e=220. The results of the elementary analysis, $^1$H-NMR, and IR are as shown below, from which it was further recognized that the obtained product was a mixture of the above-mentioned three components.

Elementary analysis: calculated (%): C 81.76, H 10.98, O 7.26, found (%): C 81.74, H 10.99, O 7.27.

$^1$H-NMR, (CDCl$_3$, TMS as internal reference, δ): FIG. 1

| | |
|---|---|
| 85.4 | cyclohexene ring, C—C=C—H pyran rings of (Ia-CH$_3$) and (Ib-CH$_3$), |
| | composite peak of C—C=C—H |
| 4.8 | pyran ring of (Ic-CH$_3$), C—C—CH$_2$ |
| 0.9–4.4 | complex multiplet (22H) |

Figure 2:
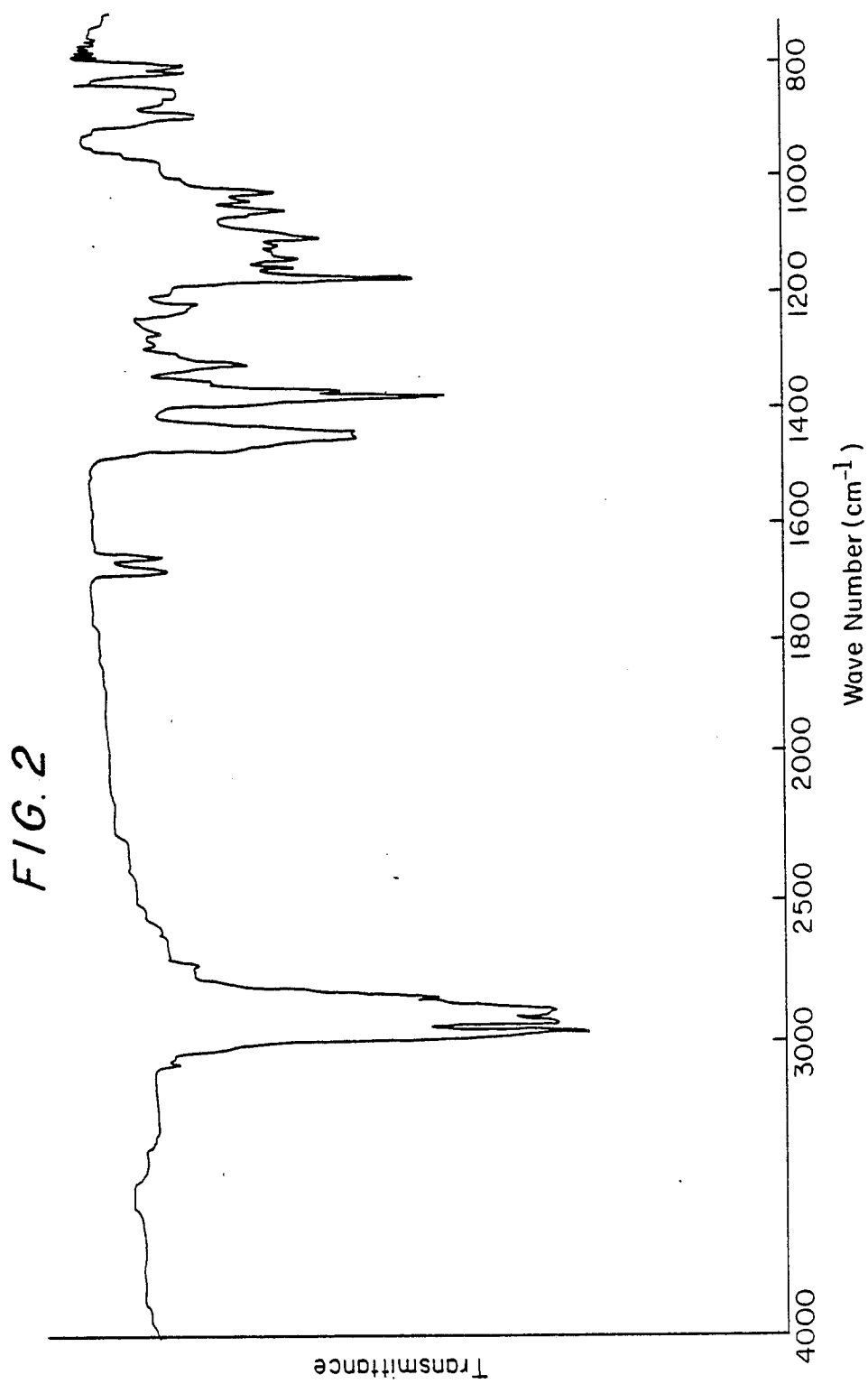
FIG. 2 is an IR spectrum of the same product.

IR (cm$^{-1}$): FIG. 2; 2960, 2930, 2900, 1675, 1650, 1440, 1375, 1320, 1220, 1170, 1100, 1055, 1025, 890, 860, 820, 805.

EXAMPLE 2

The reaction was effected in the same manner as in Example 1, except that 43 g of 3 methyl-3-buten-1-ol was used in place of 4-methyl-4-penten-2-ol. 28 g of a mixture of 6-(2,4-dimethyl-3-cyclohexenyl)-4-methyl-3,6-dihydro-2H-pyran (Ia-H), 2-(2,4-dimethyl-3-cyclohexenyl)-4-methyl-3,6-dihydro-2H-pyran (Ib-H), and 2-(2,4-dimethyl-3-cyclohexenyl)-4-methylenetetrahydropyran (Ic-H) was obtained. The product was determined by gas chromatography using Carbowax 20M (capillary column 50 m) and gas mass spectroscopy to reveal that it has a purity of 99% or more. The parent peak was found at m/e=206.

Elementary analysis: calculated (%): C 81.50, H 10.75, O 7.76, found (%): C 81.47, H 10.74, O 7.78.

EXAMPLE 3

A mixture of 238 g (1.7 mol) of 2,4-dimethyl-3-cyclohexene-1-carboaldehyde and 238 g (2.0 mol) of 4-methyl-4-penten-2-ol having a purity of 72% was added drop by drop under reflux into a mixture of 180 g of hexane and 3 g of concentrated sulfuric acid over a period of 1 hour. The water generated by the reaction was removed out of the reaction system by azeotropic distillation with hexane. The reaction was further continued for 8 hours under reflux after completing the drop by drop addition of the above reactants. The reaction product was washed with a 5% sodium carbonate solution and then with water three times. After the hexane was distilled off under a reduced pressure, the product was distilled to yield 318 g of a fraction at 100° to 120° C. at 3.5 mmHg. The fraction was subjected to precision distillation to yield 227 g of a fraction at 106° to 108° C. at 3.5 mmHg (61% yield). The results of the determination of the product by gas chromatography, gas mass spectroscopy, elementary analysis, $^1$H-NMR, and IR were completely coincident with those of Example 1.

EXAMPLE 4

Rose oil-type perfume:

| | |
|---|---|
| geraniol | 250 parts |
| citronellal | 200 |
| rosinol | 100 |
| phenylethyl alcohol extract | 310 |
| nerol | 30 |
| geranium oil Africa | 10 |
| | 900 |

100 parts of the compound obtained in Example 1 was added to 900 parts of the rose oil having the above composition, whereby a fresh and clean new rose oil was obtained.

EXAMPLE 5

Bergamot oil-type perfume:

| | |
|---|---|
| linalyl acetate | 550 parts |
| linalool | 300 |
| limonene | 30 |
| citral | 20 |
| nonyl aldehyde | 1 |
| decyl aldehyde | 2 |
| a-pinene | 5 |
| b-pinene | 5 |
| terpineol | 20 |
| coumarin | 1 |
| petitgrain paraguay | 5 |
| ocimene | 11 |
| | 950 |

50 parts of the compound obtained in Example 1 was added to 950 parts of the bergamot oil having the above composition, whereby a more natural, sweet and strong-scented bergamot oil was obtained.

The invention being thus described, it will be obvious that the same may be varied in many ways. Such variations are not to be regarded as a departure from the spirit and scope of the invention. All such modifications as would be obvious to one skilled in the art are intended to be included within the scope of the following claims.

What is claimed is:

1. A compound of the formula (I):

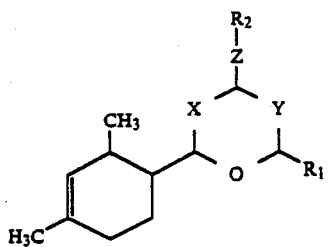

(I)

wherein $R_1$ is H or $CH_3$, $R_2$ is $CH_2$ only when Z is a double bond or $R_2$ is $CH_3$, one of the bonds X, Y or Z is a double bond and the remaining two bonds are single bonds.

2. A perfume composition, comprising:

an effective aromal amount of the compound represented by the formula (I):

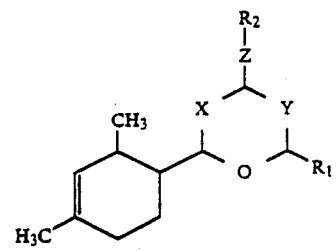

(I)

wherein $R_1$ is H or $CH_3$, $R_2$ is $CH_2$ only when Z is a double bond or $R_2$ is $CH_3$, one of the bonds X, Y or Z is a double bond and the remaining two bonds are single bonds; and an acceptable carrier therefore.

3. The perfume composition according to claim 2, wherein the perfume further comprises geranial, citronellal, rosinol, phenylethyl alcohol extract, nerol and geranium Africa.

4. The perfume composition according to claim 2, wherein the perfume further comprises linalylacetate, linalool, limonene, citral, nonyl aldehyde, decyl aldehyde, a-pinene, b-pinene, terpineol, coumarin, petitgrain paraguay and ocimene.

* * * * *